US005958399A

United States Patent [19]

[11] Patent Number: 5,958,399

[45] Date of Patent: Sep. 28, 1999

Sonderfan et al.

[54] SULFONIC ACID AND ALDEHYDE CONDENSATION POLYMERS FOR PREVENTING PREGNANCY

[75] Inventors: Andrew J. Sonderfan, Sudbury; Albert T. Profy, Cambridge; Toni Chancellor, Watertown, all of Mass.; Margo McKinlay, Barrington, R.I.

[73] Assignee: Procept, Inc., Cambridge, Mass.

[21] Appl. No.: 08/847,019

[22] Filed: May 1, 1997

[51] Int. Cl.[6] .................. A61K 31/975

[52] U.S. Cl. .................. 424/78.27; 424/486; 514/841; 514/843

[58] Field of Search .................. 514/841, 843; 424/78.27, 486

[56] References Cited

U.S. PATENT DOCUMENTS

| | | | |
|---|---|---|---|
| 3,842,088 | 10/1974 | Habeck et al. | 514/843 |
| 4,001,229 | 1/1977 | Kreighbaum | 514/843 |
| 4,416,897 | 11/1983 | Cormier | 424/315 |
| 4,419,366 | 12/1983 | Cormier | 424/321 |
| 4,432,967 | 2/1984 | Szymanski | 424/78 |
| 4,590,070 | 5/1986 | Chantler et al. | 424/78 |
| 4,604,404 | 8/1986 | Munson, Jr. et al. | 514/494 |
| 4,735,621 | 4/1988 | Hessel | 604/349 |
| 5,112,869 | 5/1992 | Watanabe et al. | 514/843 |
| 5,614,559 | 3/1997 | Singh et al. | 514/577 |
| 5,677,343 | 10/1997 | Singh et al. | 524/577 |

FOREIGN PATENT DOCUMENTS

| | | |
|---|---|---|
| 0099477 | 1/1984 | European Pat. Off. . |
| 95/14479 | 6/1995 | WIPO . |
| 96/28169 | 9/1996 | WIPO . |

*Primary Examiner*—Thurman K. Page

*Attorney, Agent, or Firm*—Hamilton, Brook, Smith & Reynolds, P.C.

[57] ABSTRACT

This invention pertains to the discovery that condensation polymers of an aldehyde and aromatic sulfonic acids and fractions thereof, such as formaldehyde naphthalenesulfonic acid condensation polymers, can prevent pregnancy in an individual.

18 Claims, No Drawings

SULFONIC ACID AND ALDEHYDE CONDENSATION POLYMERS FOR PREVENTING PREGNANCY

BACKGROUND OF THE INVENTION

Many condensation polymers of formaldehyde and aromatic sulfonic acids have been previously described. U.S. Pat. No. 4,604,404 and U.S. application Ser. Nos. 08/467,725, 08/245,619 and 08/156,443, the entire teachings of which are incorporated by reference herein, disclose the use of such polymers as antiviral agents against the Herpes simplex virus and HIV infection. However, the references do not teach or suggest the use of such polymers in preventing pregnancy.

Spermicidal formulations are popular forms of reversible contraception in the USA (Forrest, J. D. and Fordyce, R. R. *Fam. Plann. Perspect.* 20:112–118 (1988)). Most intravaginal contraceptive formulations contain the spermicide, nonoxynol-9 (N9) as the active ingredient. These formulations, typically creams, gels, or foams, are generally effective immediately upon application, and can be instilled up to approximately an hour before intercourse (Hatcher, R. A. et al., "Contraceptive Technology, 16th Revised Edition," New York, Irvington Publishers (1994)). Vaginal contraceptive films, such as "VCF" (Apothecus, Inc., Oyster Bay, N.Y.), are more recent introductions to the marketplace, at least in the USA. In contrast to other intravaginal contraceptives, films must be introduced several minutes before intercourse to ensure adequate dissolution and dispersion prior to contact with sperm.

When used alone, spermicides have a failure rate of approximately 21% (that is, typically 21% of couples using these products will experience an accidental pregnancy in the first year of use). Efficacy reportedly improves greatly when spermicides are used in combination with barrier methods, e.g., condoms (Hatcher, R. A. et al., "Contraceptive Technology, 16th Revised Edition," New York, Irvington Publishers (1994)).

SUMMARY OF THE INVENTION

This invention relates to the discovery that condensation polymers of aromatic sulfonic acids and an aldehyde and fractions thereof, particularly naphthalene-sulfonic acid formaldehyde polymers can inhibit or prevent pregnancy. Prevention or inhibition of pregnancy is defined to include, for example the prevention or inhibition of fertilization, conception or the implantation of a fertilized egg or embryo in the endometrium of the uterus in a female animal. Compounds of the present invention have been shown to have little to no vaginal irritation. Based on these findings, condensation polymers of aromatic sulfonic acids and an aldehyde and fractions thereof can be used as contraceptive agents. Thus the invention also relates to the use of the described compounds in the manufacture of a medicament for the prevention of pregnancy, or for a contraceptive.

DETAILED DESCRIPTION OF THE INVENTION

The preparation of aldehyde condensation polymers of aromatic sulfonic acids is generally known in the art. Preferred polymers possess the general structure:

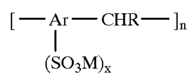

Aromatic sulfonic acids, as employed herein, include aromatic carbocyclic and heterocyclic rings substituted by one or more sulfonic acid moieties (e.g., x can be 1 to 4). Aromatic carbocyclic rings (Ar) include phenyl, naphthyl, tetrahydronaphthyl, biphenyl, phenylalkylphenyl, phenylalkenylphenyl, phenoxyphenyl, phenylthiophenyl and phenoxyalkoxyphenyl, for example. Aromatic heterocyclic rings (Ar) include, pyridinyl, pyrimidinyl, quinolinyl, thiophenyl, furanyl, pyrazolyl, imidazolyl, pyrrolyl and thiazolyl, for example. Aldehydes (CHRO) useful in the preparation of compounds for the present invention include paraformaldehyde or formaldehyde, substituted or unsubstituted acetaldehyde, propionaldehyde and benzaldehyde, for example. Preferably, the aldehyde is formaldehyde. Correspondingly, R of the formula can be hydrogen, substituted or unsubstituted alkyl (preferably lower alkyl), substituted or unsubstituted aryl (such as, phenyl). Substituents include, for example, alkyl, alkoxy, aryl, aryloxy, halogen, hydroxy, amino, alkylamino, dialkylamino, carboxyl, sulfonate and phosphonate. The polymer can be a free acid, ester or a pharmaceutically acceptable salt. Thus, M can be hydrogen, a pharmaceutically acceptable cation (e.g., an alkali metal, alkaline earth metal, or ammonium group), or a sulfonate blocking group which will preferably cleave or hydrolyze in vivo (e.g. a linear or branched alkyl). The term "polymer", as employed herein, includes any compound formed by the coupling of two or more monomers or repeating units (e.g., n is an integer of two or more). U.S. Pat. No. 4,604,404 exemplifies suitable polymers useful herein and methods of preparing them, the teachings therein being incorporated by reference. The polymers are also described in U.S. application Ser. Nos. 08/467,725, 08/245,619, and 08/156,443, the entire teachings are incorporated by reference herein.

A particularly preferred polymer is the condensation product of a naphthalene sulfonic acid and formaldehyde of the formula:

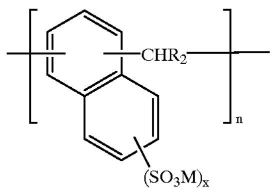

Wherein x is 1 or 2; $R_2$ is hydrogen, alkyl, alkoxy or an anionic group, such as carboxyl and phosphonate; M is hydrogen or a pharmaceutically acceptable cation. In some instances, one or more of the sulfonic acid groups can be irreversibly blocked.

The polymers of the present invention also include copolymers wherein the aldehyde and/or aromatic sulfonic acid are added as mixtures of different aldehydes and/or aromatic sulfonic acids (such as those defined above). Also included are copolymers wherein an aromatic group, not substituted by sulfonic acid, is added. For example, the aromatic group can be a carbocyclic or heterocyclic group (as defined above) unsubstituted or substituted by one or more groups, such as alkyl, alkoxy, aryl, aryloxy, halogen, hydroxy, sulfonamide, carboxyl or phosphonate.

It is preferred that the molecular weight of the polymer (MW) be less than about 50 kDa and/or greater than about 0.7 kDa. More preferred are polymers with a molecular weight between from about 1.3 to about 30 kDa, or between from about 4 to about 12 kDa. A particularly advantageous polymer is a 5±1 kDa condensate of 2-naphthalene sulfonic acid and formaldehyde.

Preferably, the average number of sulfonic acids per aromatic group is between about 0.5 to about 2.0, most preferably about 1.0.

The narrow or mono-dispersed molecular weight polymers can be prepared by fractionation methods generally known in the art (see, e.g., *Polymer Fractionation*, Editors, Cantow and Manfred, Jr., (Acad. Press) 1967), such as solvent precipitation, gel permeation chromatography, salt precipitation and diafiltration. Alternatively, the polymers can be manufactured by the stepwise or controlled condensation of naphthalenesulfonic acid and formaldehyde.

A "narrow-dispersed polymer" is defined as a polymeric composition wherein the species thereof possess substantially the same molecular weight. For example, a narrow-dispersed polymer includes polymeric compositions wherein the polydispersity is less than about 2, preferably less than about 1.5 and more preferably less than about 1.2. A "mono-dispersed polymer" is defined as a polymeric composition wherein substantially all of the species thereof possess a single molecular weight, such as a tetramer, pentamer, hexamer, heptamer, octamer, nonamer, etc.

As described above, the condensation polymer can, optionally, be administered as a pharmaceutically acceptable salt. Examples of suitable salts include the alkaline, alkali metal and ammonium salts, such as calcium, sodium, potassium, ammonium and alkyl or aryl ammonium salts (such as trimethylammonium, triethylammonium and triethanolammonium (trolamine) salts).

The preparation or polymer of this invention can be administered intravaginally (e.g., contraceptive formulation, suppository or lubricant) in dosage formulations containing a physiologically acceptable vehicle and optional adjuvants and preservatives. Suitable formulations include physiologically acceptable gels, foams and creams. Vehicles include saline sterile water, Ringer's solutions, and isotonic sodium chloride solutions. Specifically, Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP can be used, for example. In another embodiment, the compound is composed in, applied to or sprayed on, e.g. as a film, a contraceptive device, such as a condom (including male condoms and female condoms, as in the REALITY female condom (Women's Health Company), U.S. Pat. No. 4,735, 621) or diaphragm. The specific dosage level of active ingredient will depend upon a number of factors, including biological activity of the particular preparation and the general health of the patient or individual.

Typically, the compound will be formulated in a gel at a concentration of between about 0.5% to about 50%, preferably between about 1% to about 10% (w/w). Gelling agents for pharmaceutical formulations are generally known in the art. For example, the gelling agent can be hydroxyethyl cellulose (such as Hydroxyethyl Cellulose 250 HHX, (Natrosol)), guar gum, cellulose gum, crosslinked polyacrylic acid (such as, Carbopol 1342, Carbomer 974B, Carbomer 980, Carbomer 910, Carbomer 1382), or Theronic poloxymer. A particularly preferred gelling agent is Carbomer 1382, a copolymer of acrylic acid and a long chain methacrylate crosslinked with allylethers of pentaerythritol. The agent is generally added in an amount between about 1 to about 5% by weight.

The compound or formulation is generally administered prior to or after sexual intercourse (e.g. up to an hour before or twelve hours after intercourse), such as immediately prior to or after sexual intercourse (e.g. within 30 minutes before to one hour after intercourse). The compound can be administered overtly (with the consent of a male partner) or covertly (without the cooperation or consent of a male partner).

Advantageously, the compound is administered in an amount which is effective to function not only as a contraceptive, but also as an antiviral or antibacterial agent (e.g., at an amount which inhibits HIV infection or herpesvirus infection or other sexually transmitted diseases). Other antiviral agents that interfere with HIV viral replication can be administered in conjunction with this preparation, according to the methods of this invention with synergistic results in some instances. Co-administration of antiviral agents can effectively inhibit various stages of the virus life cycle, thus optimizing the therapeutic benefit of the preparation of this invention, for reducing or eliminating viral infectivity and the symptoms associated therewith. For example, HIV reverse transcriptase inhibitory agents (such as, azidothymidine (AZT), dideoxyinosine (ddI) lamivudine, stavudine or PMPA), uncoating inhibitors (bicyclam), integration, transcription, or translation inhibitors (antisense oligonucleotides), other fusion/binding inhibitors, assembly/release inhibitors (e.g., interferon), HIV protease inhibitors (such as Saquinavir, Indinavir, Ritonavir, Nelfinavir, VX-478, or non-nucleoside reverse transcriptase inhibitors (such as, delavirdine or nevirapin) can be co-administered with the condensation polymer separately or as a single dosage formulation containing the condensation polymer and other anti-viral agent(s).

The invention can also be administered in conjunction with additional contraceptive formulations, such as nonoxynol-9, octoxynol, chlorohexidine, benzalkonium chloride and menfegol.

The invention has advantages over other methods for inhibiting conception in that it does not exhibit risk of breakage failure under conditions of risk (as in male and female condoms), does not require the cooperation and/or consent of the male partner (as in male and female condoms), is not associated with adverse effects upon the reproductive tract (as in intrauterine devices), can additionally be effective in the prevention of sexually transmitted diseases (STDs, not shown with spermicides and oral contraceptives), does not require daily administration for efficacy (as in oral contraceptives), and is generally not systemically absorbed, thereby avoiding side effects attributed to systemic administration (as in oral contraceptives).

The invention will be further illustrated by the following non-limiting exemplification:

EXEMPLIFICATION

Example 1

Synthesis of Condensates: Polymerization

A mixture of 2-naphthalenesulfonic acid sodium salt (1.15 g, 5 mmol), 37- aqueous formaldehyde (0.65 ml, ~6 mmol), and sulfuric acid (0.7 g concentrated sulfuric acid in 0.5 ml of water) was heated at 98° to 100° C. for 43 hours. The reaction mixture was then diluted with water (30 ml), neutralized with calcium carbonate to pH 7 and filtered, the filtrate was evaporated to dryness to yield 1.22 g of the polymer condensate.

The above experiment was repeated modifying the reaction parameters as exemplified in Table 1.

TABLE 1

| Example | HCHO (eqv) | Water (ml) | Temp (° C.) | Time (h) | Product size (kDa) | | |
|---|---|---|---|---|---|---|---|
| | | | | | Mp | MWd | MW |
| 1* | 1 | 0.5 ± 1 | 96–104 | 45 | 6.0 | 0.7–150 | 16 |
| 2* | 1 | 1.5 + 0.5 | 103–107 | 52 | 25 | 0.2–100 | 13 |
| 3* | 1 | 2 ± 0.5 | 100–103 | 54 | 2.0 | 2–200 | 12 |
| 4* | 1 | 2 + 1 | 100–105 | 44 | 0.4 | 0.3–175 | 9 |
| 5 | 1 | 1.5 | 95–100 | 44 | 2.0 | 0.4–90 | 9 |
| 6 | 1 | 1.5 | 100–105 | 53 | 4.0 | 0.4–100 | 14 |
| 7 | 1 | 2 | 105–110 | 92 | 8.0 | 3–100 | 14 |
| 8 | 1 | 0.5 | 96–105 | 72 | 21 | 0.1–980 | 56 |
| 9 | 1 | 1.5 | 120–125 | 6 | 0.2 | 0.2–10 | 2 |
| 10 | 1 | 1.5 | 120–125 | 8 | 0.2 | 0.3–15 | 2 |
| 11 | 1 | 1.5 | 120–125 | 15 | 3.0 | 0.3–100 | 4 |
| 12 | 1 | 1.0 | 120–125 | 8 | 3.0 | 0.4–80 | 14 |
| 13 | 0.5 | 1.5 | 98–100 | 48 | 3.0 | 0.4–100 | 11 |
| 14 | 0.75 | 1.5 | 98–100 | 24 | 4.0 | 1–120 | 18 |

*Open vessel reactions;
Mp = peak molecular weight;
MWd = molecular weight distribution;
MW = molecular average weight Example 15

Synthesis of Condensation Polymer of 2-naphthalenesulfonic Acid and Formaldehyde A mixture of 5.7 g of 2-naphthalenesulfonic acid, sodium salt (23 mmol) was combined with ~3 ml of 37% formaldehyde (~43 mmol), 1.9 ml of concentrated sulfuric acid, and 5 ml of water was combined and heated in a sealed tube for ~24 hours at 120–130° C. The reaction mixture is diluted with water (~20 ml) and neutralized to pH=7 with NaOH. The neutralized reaction can be concentrated to dryness to obtain ~11 g, which consists of the condensate and salts.

Synthesis of Condensates: Stepwise

Example 16

5-Bromo-2-naphthalenesulfonic acid

5-Amino-2-naphthalenesulfonic acid (11.15 g, 50 mmol) was dissolved in 100 ml of 0.5 N NaOH solution with stirring. The dark-red solution was cooled down to 0° C. by addition of ice (~100 g). Before the ice completely dissolved, 20 ml of 40% HBr aqueous solution was added dropwise and the resulting suspension was maintained at −5° to 0° C., then 10 ml of $NaNO_2$ (3.65 g) aqueous solution was added in 30 minutes. The mixture was stirred continuously for 30 minutes at −5~0° C. The unreacted $NaNO_2$ was decomposed by addition of 350 mg of urea at the end of reaction. The resulting dark diazonium suspension was kept below 0° C., and added dropwise over one hour period to CuBr (7.15 g) solution in 40 ml of 40% HBr at 70° C. with vigorous stirring (the CuBr solution was in a 1000 ml flask). The dark mixture was stirred at 80° C. for 40 minutes, then cooled down to room temperature and treated with 200 ml of water. The precipitate was collected in a Buchner funnel and washed with about 50 ml of water. 13.9 g of crude product was obtained after drying under vacuum. The crude compound was refluxed in 500 ml of water for 2 hours, cooled to room temperature and filtered. The filtrate was evaporated to dryness and solid dried in vacuo to yield 8.23 g (57% yield) of pure product.

The purity of product was checked with reverse phase HPLC and $^1$H-NMR (250 MHz).

Example 17

8'-Methylen-bis-5-bromo-2-naphthalene-sulfonic acid (sodium salt)

A mixture of 5-bromo-2-naphthalenesulfonic acid (17.22 g), TFA (200 ml), Amberlyst-15 resin (17 g, Aldrich), paraformaldehyde (4.5 g) and $H_2O$ (50 ml) was heated at 130° C. for 14 hours in a closed thick-wall tube. After cooling to room temperature, the mixture was filtered in a Buchner funnel and, the collected solid was washed with about 10 ml of TFA, dissolved in 250 ml of methanol/water (4/1) and filtered. The filtrate was evaporated to dryness and the solid was suspended in 80 ml of water, neutralized to pH ~8 with 10 M NaOH. The solid was filtered, washed with 60 ml of acetone and dried in vacuo overnight. 15.03 g (80% yield) of pure product was obtained.

Example 18

8,8'-Methylen-bis-2-naphthalenesulfonic acid

A suspension of 8,8'-methylen-bis-5-bromo-2-naphthalenesulfonic acid (sodium salt, 6.30 g), NaOH (0.32 g) in 300 ml of MeOH, was slowly added with Pd—C (10%, 5.0 g) under argon atmosphere. The suspension was shaken at 50 psi of $H_2$ for 18 hours. Then the mixture was filtered and the filtrate was passed through a column packed with ~20 g of IR-120 resin. The solvent was removed on rotavap, and the residue was dissolved in 200 ml of water then filtered again. The filtrate was neutralized with 5 M NaOH to pH ~7 and concentrated to ~50 ml volume, then 300 ml of acetone was added slowly with shaking. The resulting white precipitate was collected in a Buchner funnel, washed with 20 ml of acetone and dried in vacuo to result in 3.51 g of dry product (sodium salt).

Examples 19 and 20

Oligomerization for Tetramer and Hexamer, Respectively 5.11 g of sodium salt of dimer was converted into free acid by passing through IR-120 resin column in water. Water was removed on rotavap and the residue was again dissolved in 10 ml of water and transferred into 50 ml of TFA in a thick-wall flask, then paraformaldehyde (0.195 g) was added and the flask was sealed. The solution was stirred at 60° C.–65° C. for 15 hours. The solvent was removed and the residue was dissolved in methanol, coated on silica gel and subjected to flash silica-gel column (EM Science, silica gel 60 F-254, 230–400 mesh for column), where the elution was started with 16:1:1 of THF:MeOH:$H_2O$ to 5:1:1 final ratio.

The solid from tetramer fraction was neutralized to pH ~7 with 5 M NaOH in 5 ml of water, added with 5 ml of MeOH and 125 ml of acetone to afford 0.94 g of precipitate. The salt was converted into free acid by passing through IR-120 resin and 0.73 g of dry tetramer was obtained.

From the hexamer fraction, 0.21 g of hexamer was obtained by the same method as that described for tetramer.

3.5 g of starting material (dimer) was recovered from the first fraction.

Example 21

Octamer

A mixture of tetramer (130 mg), Amberlyst-15 resin (150 mg), water (0.4 ml), and 2 ml of TFA solution of paraformaldehyde (1 mg/ml) was stirred at 85° C. for 15 hours in a sample vial closed with a teflon cap. The reaction mixture was cooled to room temperature, diluted with 5 ml of water and filtered. The filtrate was evaporated to dryness, dissolved in methanol, and coated on silica gel, then passed through a flash column where tetramer was eluted with 6:1:1 of THF:isopropanol:$H_2O$, and octamer was eluted with MeOH:$H_2O$ (85:15). From the later fraction, 50 mg of crude octamer was obtained.

The crude octamer was passed through IR-120 resin, purified by reverse phase prep HPLC and 15 mg of octamer (96.6% pure by analytical HPLC) was obtained.

Example 22

Size Exclusion Chromatography

Aliquots of synthetic polymer solutions were fractionated by size using a Waters M625 pump, M996 diode array detector, Millenium software system and either two 6 μm 250 angstrom Waters Ultrahydrogel columns (7.8×300 mm; mobile phase flow 1 ml/min) or a 17 μm TosoHaas G3000PW column (21.5×600 mm) coupled with a TSK-Gel Guard PWH column (21.5×75 mm; flow rate 3 ml/min). The mobile phase consisted of 0.2 M ammonium acetate (pH 6.2) made from glacial acetic acid (Baker Analyzed HPLC Reagent) and ammonium hydroxide (25%, Mallinckrodt) and 35% acetonitrile (B&J Brand). Prior to use, the mobile phase was filtered through a 0.45 μm nylon membrane and sparged under Grade 5 helium. A solution of the synthetic samples at 2.2–10 mg in up to 200 μl MilliQ water was injected onto the Ultrahydrogels or 40–300 mg in up to 2 ml MilliQ water mobile phase (50:50, v/v) was injected onto the TosoHaas columns following ultrasonicating (Branson 2200), vortexing and filtering (0.45 μm Acrodisc, Gelman Sciences). Collected fractions were pooled according to elution time. Superimposable chromatographic profiles by absorbance measurements were demonstrated with replicates and the solvent was removed using Savant speedvacs at high temperature (either SC200 and Vapornet VN100 or Plus SC210A). The residue was redissolved in water and redried to remove trapped solvent. The material was weighed, dissolved in water and normalized to stock concentrations using absorbance measurements at 290 nm versus standards.

Example 12, Table 1 above, was fractionated in this manner to obtain polymer fractions possessing a peak molecular weight (Mp) of 31 kDa (average molecular weight (MW) of 38 kDa); an Mp of 16 kDa (MW of 22 kDa); an Mp of 10 kDa (MW of 15 kDa); and an Mp of 5.6 kDa (MW of 10 kDa).

Example 23

Light Scattering Methodology

The samples were subjected to analytical HPLC using a Waters 625 pump/modified 410 RI detector that contained inside a PD2000 laser light scattering intensity detector (Precision Detectors, Inc., Amherst, Mass.). This system was equipped with a Waters Ultrahydrogel 250 aqueous GPC column (7.8 mm I.D.×300 mm, 250 Å pore size, $8\times10^4$ exclusion limit, PEO). The mobile phase consisted of 65% 0.2M ammonium acetate pH=6.5/35% acetonitrile in an isocratic mode with a flow rate of 1 ml/min. Elution was monitored by RI, low (15°) and high (90°) angle light scattering and absolute molecular weight ranges were obtained from this information.

Example 24

Fractionation of Polymer

The salts from the neutralization process were removed from the polymer produced in Example 15 through a fractionation process by addition of a polar organic solvent (acetone, ethanol, or methanol). An aqueous solution of the final reaction mixture (~10 g/ 20 ml) was treated with incremental amounts of organic solvents. Initial organic solvent caused the dissolved salts to form a lower layer.

Once the majority of the salt was removed, fractionation of the material into more homogeneous molecular weight ranges occurred. Additional solvent was added to form a lower, darker layer. The volume of organic solvent added was determined by monitoring the two phases by GPC/LS. In general, the higher molecular weight material was moved into the lower layer and the lower molecular weight material remained in the upper layer.

When the desired molecular weight range was identified, it was isolated in one of several ways. The first method was to simply remove all volatile solvent from the material (by a combination of rotary evaporation under reduced pressure and vacuum oven). The second method was to disperse the solution of the product into a large excess of a polar organic solvent (acetone, ethanol, or methanol) and collect the resulting solid by filtration.

Material prepared according to the above reaction description and fractionation process yielded several narrow range molecular weights (~3K, ~5K, ~10K, ~25K, EX 15/3, EX 15/5, EX 15/10 and EX 15/25, respectively).

Example 25

The sodium salt of 2-naphthalene sulfonic acid (1000 g) was added to a glass reactor with 8925 ml ethanol, 3800 ml deionized water and 10 g of carbon. The mixture was heated to approximately 78° C. and filtered through celite. The mixture was cooled to ambient temperature and held for about 6 hours. The wet crystals were collected by filtration and dried in a vacuum oven (80° C./25" vacuum) to a constant weight. Average yield was 59%.

The recrystallized 2-naphthalene sulfonic acid (1000 g as prepared above) was then combined with water (866 g) and 99% sulfuric acid (330 ml). The reactor was sealed and heated with agitation to about 105° C. over a 130° C. oil bath. Formaldehyde (502 g, 37% aqueous solution) was added to the reactor over 45 minutes. The reactor was maintained for about 10 hours. Over the course of reaction, the internal pressure rose to about 11 psi.

After completion of the reaction, the contents of the reactor were cooled and diluted with 500 g of deionized water. The pH was adjusted from less than about 1 to a pH of about 7 by the adding about 500 g NaOH. The reaction yielded at least about 90% unfractionated polymer.

The salts from the neutralization process were removed by fractionation by the addition of 10 l acetone, resulting in the formation of two layers. The lower layer was discarded. To the upper layer, 2 l of acetone were added, resulting again in two layers, the upper layer of which was discarded. About 600 g of water was added to the lower layer with about 1.4 l of acetone, again resulting in the formation of two layers. The lower layer was discarded, the upper layer transferred and treated with about 1.2 l of acetone. The upper layer formed was discarded and about 520 ml of water was added to the lower layer. The solution was concentrated and transferred to a vacuum oven and dried at 80° C./24" of vacuum to a constant weight. Fractionation was monitored by GPC/LS. The process yielded the condensation polymer, molecular weight between about 4000–6000 daltons (average 11% yield).

Example 26

The specified quantities of Example 25 (100 aqueous solution), purified water (USP), and lactic acid (1% aqueous solution (w/w)) was mixed thoroughly in the amounts set forth in Table 2. During mixing, the stated quantity of Carbomer 1382 (BF Goodrich, Cleveland, Ohio) was added and agitation was continued until the Carbomer was hydrated. A 50% aqueous solution (w/w) of Trolamine (Spectrum, New Brunswick, N.J.) was added, with mixing. The pH was monitored.

TABLE 2

| Reagent | Vehicle | Vehicle | 0.1% Gel | 0.5% Gel | 1.0% Gel | 4.0% Gel | 4.0% Gel |
|---|---|---|---|---|---|---|---|
| Formulation | 1 | 2 | 3 | 4 | 5 | 6 | 7 |
| Polymer (g) | none | none | 18.5 | 34.093 | 165.0 | 860.0 | 268.5 |
| Purified Water (g) | 6201.91 | 2548.0 | 1665.0 | 6234.26 | 1336.5 | 1096.5 | 5855.44 |
| Lactic Acid (g) (1% sol'n) | 3.60 | 140.0 | 92.6 | 3.64 | 82.5 | 107.5 | 3.60 |
| Carbomer 1382 (g) | 63.0 | 56.01 | 37.09 | 86.4 | 33.0 | 43.01 | 126.0 |
| Trolamine (g) (50% sol'n) | 31.5 | 56.0 | 37.02 | 43.5 | 33.0 | 43.0 | 63.0 |
| pH (Initial) | — | 2.89 | 2.94 | — | 3.03 | 3.52 | — |
| pH (Final) | — | 4.73 | 4.93 | — | 4.66 | 4.60 | — |

The gels were filled into ⅝×3 inch epoxy-lined aluminum, blind end tubes with polypropylene caps and special No. 16 neck size (Montebello). The fill amount was approximately 3.7 g. The tubes were sealed And then sterilized in an autoclave at 121° C. for 20 minutes.

Example 27

Biological Activity

The potential irritant effects of 0.1%, 1% and 4% (Formulations 3, 5 and 6) concentrations of polymer, as formulated above, (PRO 2000 gel) were evaluated in the vaginas of New Zealand White rabbits. Five rabbits in each of 5 groups received a daily 1-ml dose of PRO 2000 gel, a vehicle gel (Formulation 2), or a 4% formulation of nonoxynol-9 (Conceptrol®; included for comparison) in the vaginal vault. The treatment was repeated for 14 consecutive days. One day after the last dose, rabbits were euthanized and the vaginal tissue was removed for histopathological evaluation. All rabbits survived and exhibited no clinical signs of systemic toxicity nor external signs of irritation. Rabbits generally gained weight during the study. The histopathological irritation scores were graded as mild in each treatment group, and were well within the acceptable limits of this test.

The effect of the PRO 2000 gels on pregnancy outcome was studied in artificially inseminated rabbits. Four groups of ten female rabbits each were dosed intravaginally with a vehicle gel (Formulation 1), a 4% formulation of nonoxynol-9 (Conceptrol®), 0.5% PRO 2000 gel (Formulation 4) or 4% PRO 2000 gel (Formulation 7). Rabbits were dosed once daily (1 ml/dose) from the day prior to artificial insemination through gestation day 7. On gestation day 0, does were dosed and then inseminated 15–30 minutes later with 0.5 ml of diluted semen collected from fertile bucks. On gestation day 19, does were euthanized and necropsied, their pregnancy status was noted, and (for each pregnant rabbit) the number of corpora lutea, fetuses, and implantation sites was recorded. The positive control, (Conceptrol®) was contraceptive in this experiment: Nine of ten rabbits in the Conceptrol® group were not pregnant. The vehicle gel had no effect on pregnancy outcome: Two of ten rabbits in the vehicle gel group were not pregnant, a fraction consistent with this laboratory's success rate for conception following artificial insemination (85–90%). When compared with the vehicle gel group, fewer animals given 4% PRO 2000 gel were pregnant: three of ten rabbits. Administration of 0.5% PRO 2000 gel had no effect on the number of rabbits that became pregnant: nine of ten rabbits were pregnant. These results were obtained on the date when rabbits were necropsied to evaluate pregnancy status.

The pure drug substance was evaluated for its ability to inhibit hyaluronidase, an enzyme that facilitates penetration of the cumulus layer which is necessary for binding of a spermatozoon to the oocyte. Hyaluronidase activity was quantified by measuring the extent of hyaluronic acid hydrolysis in the presence of various concentrations of the polymer of Example 25. Enzyme was pre-incubated with test agent for 10 minutes, then reactions were started by addition of substrate. Thirty-minute incubations were carried out at ambient temperature, then the reaction product was determined calorimetrically. The IC50 of the polymer was determined to be approximately 6 μg/ml. The polymer was found to be a highly effective, apparently irreversible hyaluronidase inhibitor. It is not yet known if this property contributes to contraceptive efficacy.

PRO 2000 gel (4%) was evaluated for compatibility with latex condoms. Using standard test methods, airburst and physical properties of non-lubricated, latex condoms were evaluated immediately after unwrapping, or after exposure to 4% PRO 2000 gel (30 minutes at 37° C., 95% relative humidity). The gel did not affect the properties of the condoms.

EQUIVALENTS

Those skilled in the art will recognize, or be able to ascertain, using no more than routine experimentation, many equivalents to the specific embodiments of the invention described specifically herein. Such equivalents are intended to be encompassed in the scope of the following claims:

We claim:

1. A method of preventing pregnancy in an individual in need thereof, comprising vaginally administering to the individual an effective amount of a composition comprising a condensation polymer of an aromatic sulfonic acid and an aldehyde or a pharmaceutically acceptable salt thereof in a physiologically acceptable carrier, wherein the composition is administered prior to or after sexual intercourse.

2. The method of claim 1 wherein the condensation polymer is a condensation polymer of a naphthalene sulfonic acid and formaldehyde.

3. The method of claim 2 wherein the condensation polymer is a narrow or mono-dispersed condensation polymer.

4. The method of claim 2 wherein the condensation polymer has a molecular weight of less than about 50 kDa.

5. The method of claim 4 wherein the condensation polymer has a molecular weight between from about 0.7 kDa and about 50 kDa.

6. The method of claim 5 wherein the condensation polymer has a molecular weight between from about 1.3 kDa to about 30 kDa.

7. The method of claim 6 wherein the condensation polymer has a molecular weight between from about 4 kDa to 12 kDa.

8. The method of claim 2 wherein the condensation polymer has an average of between about 0.5 to about 2.0 sulfonic acid groups per aromatic group.

9. The method of claim 8 wherein the condensation polymer has an average of about 1 sulfonic acid group per aromatic group.

10. The method of claim 1 wherein the composition is administered immediately prior to sexual intercourse.

11. The method of claim 10 wherein the composition is a gel, cream or foam.

12. The method of claim 11 wherein the composition is a gel.

13. The method of claim 11 wherein the polymer is present in the composition in a concentration between about 1 and about 10% by weight.

14. The method of claim 13 wherein the polymer is present in the composition in a concentration of about 4% by weight.

15. A method of preventing pregnancy in an individual in need thereof comprising vaginally administering to the individual a gel comprising between about 1% to about 10% by weight of a condensation polymer of a naphthalene sulfonic acid and formaldehyde, wherein the composition is administered prior to or after sexual intercourse.

16. The method of claim 15 wherein the polymer has a molecular weight of about 5 kDa.

17. The method of claim 1, wherein the composition is administered between about 1 day prior to and about 7 days after sexual intercourse.

18. A method of preventing pregnancy in an individual in need thereof, comprising vaginally administering to the individual an effective amount of a composition comprising a condensation polymer of an aromatic sulfonic acid and an aldehyde or a pharmaceutically acceptable salt thereof in a physiologically acceptable carrier, wherein the composition inhibits hyaluronidase.

* * * * *